OAK TREE
Filed Oct. 23, 1973 3 Sheets-Sheet 1
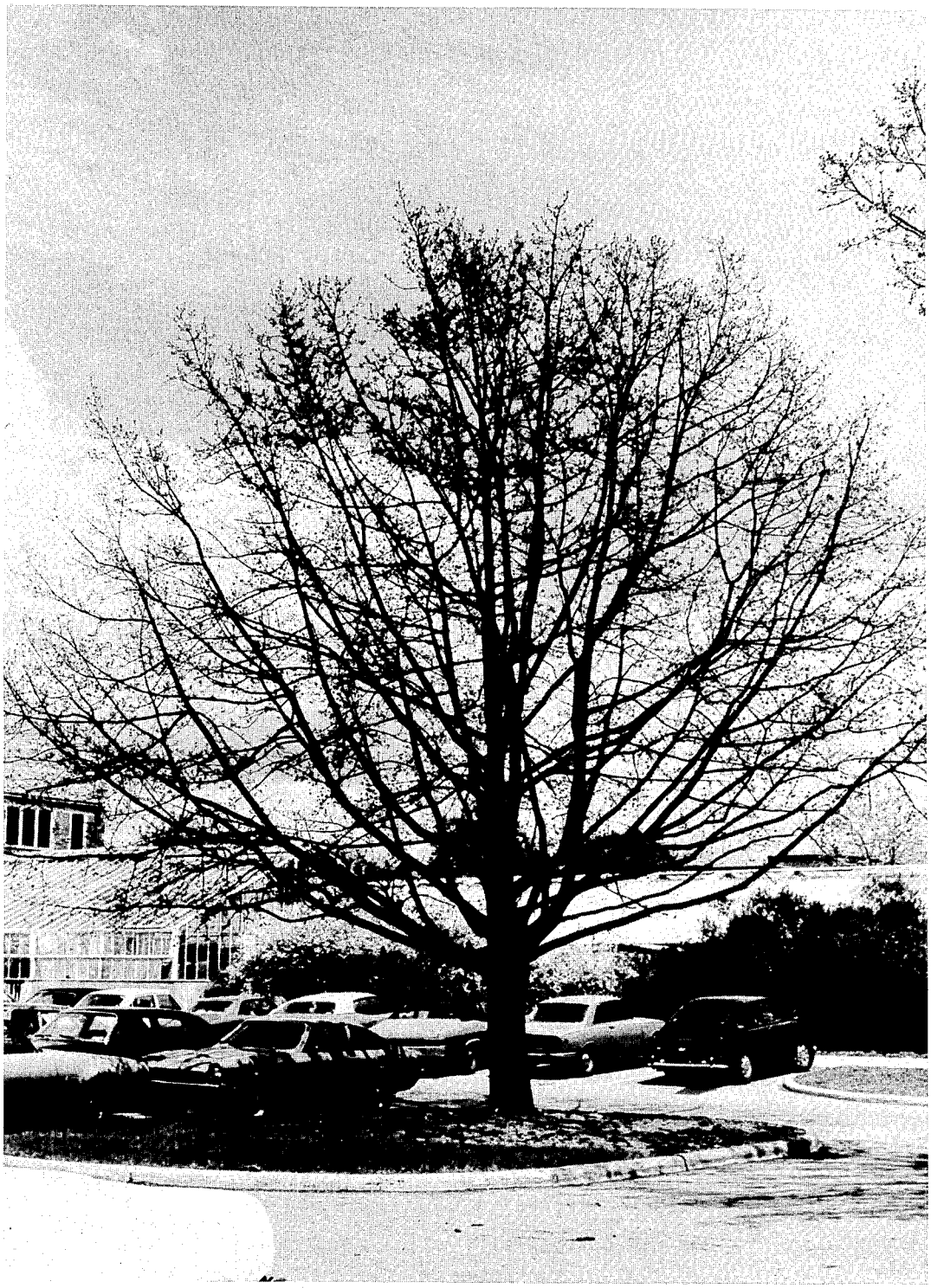

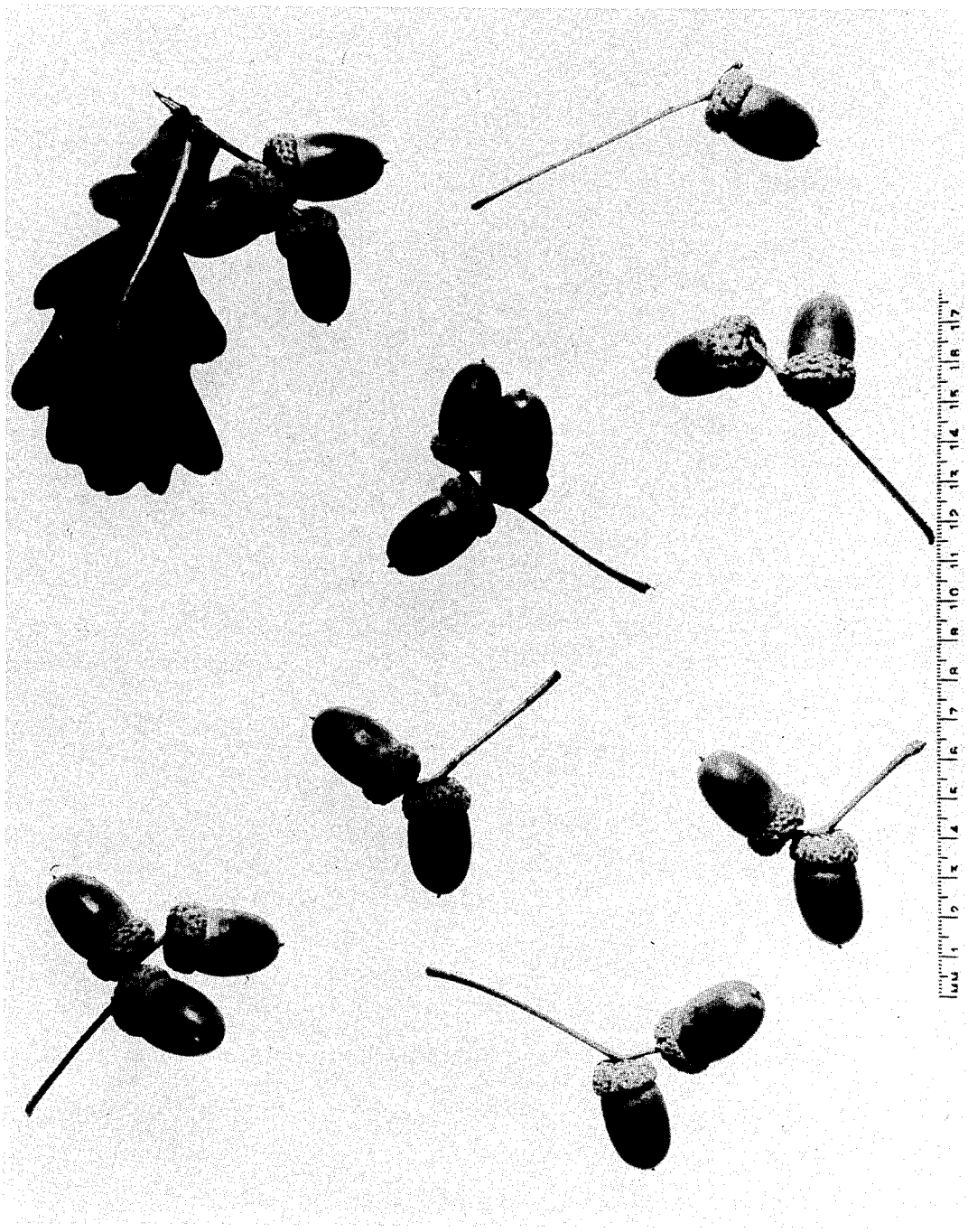

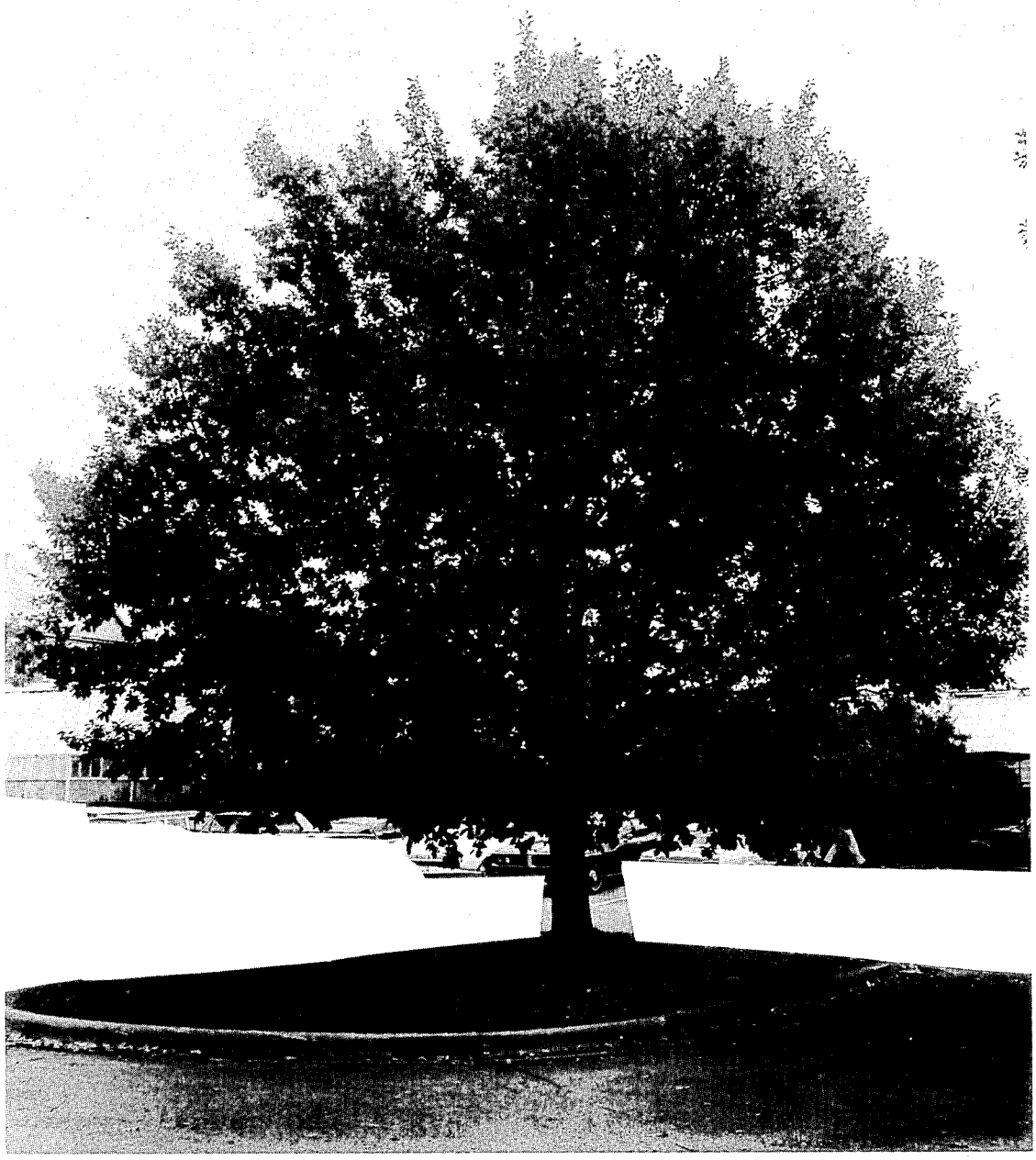

United States Patent

Plant Pat. 3,708

Patented Apr. 22, 1975

3,708

OAK TREE

Milton Baron, Haslett, Mich., assignor to J. Frank Schmidt and Son Co., Troutdale, Oreg.

Filed Oct. 23, 1973, Ser. No. 408,830

Int. Cl. A01h *5/12*

U.S. Cl. Plt.—51 1 Claim

The present invention relates to a new and distinct variety of English oak tree of the species botanically known as *Quercus robur*, which was discovered and developed by me as a selected cultivated seedling of unknown parentage, among a group of plants of this species being grown under my supervision and control at Michigan State University at East Lansing, Mich.

Over many years, the University has collected or received by gift, or otherwise reproduced, many seedling shade trees, and the present new English oak seedling, among hundreds of others (many grown from acorns produced thereby), have been undergoing tests and experimental developments in the University Campus Nursery and on the campus grounds at East Lansing since 1946. When the Dutch Elm Disease (DED) became epidemic in this area starting about 1961, these English oak seedlings were even more closely scrutinized as likely substitutes for American elms. Over this extended period of observations, four salient traits bearing on the overall landscape suitability of the English oak have emerged:

A. Ease of transplanting in late winter or spring;
B. Low maintenance qualities as manifested by
   (a) exceptional ability to withstand severe environmental stress resulting from compacted soil, restricted root run, extended drought, gale winds and ice storms;
   (b) absence of any need over a period of nearly three decades to initiate programs to control insects or disease;
C. Long-persisting foliage casting effective shade until late October (and later farther south); and
D. Pronounced variability in form and growth rate, the latter varying 300% from about 6 inches to over 18 inches annually.

The first three of these traits (A, B, and C) qualify the English oak (including the instant variety) as a prime candidate for urban plantings requiring many individuals of one kind, such as boulevard and street plantings.

The fourth trait (D) in equally decisive fashion precludes the English oak from assuming its rightful place among the finest of trees or urban planting when grown from seeds (acorns). Because of its notorious variability, it simply cannot be recommended for any use where landscape specifications demand uniform crown proportions and growth rate in order to achieve integrated landscape design. Furthermore, this variability is evident even among seedling progeny from a single seed parent, as demonstrated by marked differences in growth rate observed among 9,000 two-year old seedlings grown by me from a single high-producing campus tree in 1964.

Finally, seedlings from acorns produced within the range of our native *A. alba* and *Q. macrocarpa* have the potential for an even wider range of variability as illustrated by several putative hybrids that have also been grown by me on the University campus aforesaid.

Clearly then, the English oak cannot fulfill its great promise in the absence of asexual propagation. Such propagation of a superior selected variety, tailored to perform a specific landscape role, and made economically feasible by patent protection, constitutes a first step in converting the notorious variability of this species from a handicap to a virtue. Vegetative propagation of the instant variety provides an ecologically, practically and esthetically ideal candidate for any landscape application requiring an integrated planting of trees having expansive, low-profile crowns.

As the result of my prolonged observations and tests, I am convinced that the selected seedling which is the subject hereof is definitely a new and distinct variety, as particularly evidenced by the following unique combination of primary characteristics which are outstanding therein and which distinguish the same from all other varieties of English oak tree of which I am aware:

(1) An expansive three with a broadly hemispherical crown having a height/width ratio of 0.76;
(2) Main scaffold branches all arising in the lower third of the crown, trending upward at about 60° from the vertical;
(3) The upper two-thirds of the trunk bearing only small branches and thus playing a minor role in the structural framework of the crown;
(4) Sturdy wide-angle crotches averaging about 66°;
(5) Attractive leathery leaves with a faint waxy bloom and being bluish-green on both surfaces; and
(6) Extremely heavy fruit production which, in some years, amounts to 200 pounds or more.

Of the distinguishing characteristics noted above, half deal with the distinctive internal structure of the crown, which are features of great concern from the standpoint of maintenance requirements and longevity. In point of origin, the main branches are reminiscent of *Q. robur* "Fastigiata," but there the similarity ends. In the instant tree, the crotches are more than 5 times as wide and therefore capable of withstanding much greater strain, while the main branches are much shorter and more spreading and have well-developed secondary branches.

Asexual reproduction of my new seedling by soft budding on potted 2-year seedlings, as performed under my direction and supervision at the Beaumont Nursery of Michigan State University, shows that the foregoing characteristics and distinctions come true and are established and transmitted through succeeding propagations.

The accompanying drawings show typical mature tree specimens of my new English oak variety while in foliage as well as bare of foliage, and also a typical specimen leaf and typical specimens of the fruit (acorns).

The following is a detailed description of the new variety, with color terminology in accordance with general color terms of ordinary dictionary significance, since the color features are not materially significant or different from those normal to the species:

A large expansive tree with a crown height/width ratio of 0.76 and rugged lower branches forming the main elements of the crown; crotches diverging from the trunk at an angle averaging 66°, the angle of branch ascent gradually narrowing to about 60°; bark dark, deeply furrowed, forming irregular plates; twigs glabrous, the second year wood being gray-brown and the current year greenish-brown; buds obscurely 5-angled, glabrous except for the sparsely villous scale margins; leaves glabrous, blade rather leathery, with a faint bloom, and being blue-green above, paler below, obovate, mostly 11–16 (9.3–18.5) cm. long and 7–10 (5.4–13.0) cm. wide, pinnately lobed, with 3–7 pairs of rounded lobes separated by shallow rounded sinuses reaching less than half-way to the midrib, auriculate at base, the falcate mostly symmetrical appendages typically clasping the 4–7 mm. long petiole; fruits abundantly produced, in clusters of 1–3 (averaging more than 2) on a relatively stout peduncle about 2 mm. in diameter and mostly 3–4 (2.5–5.5) cm. long, with the acorn being lustrous brown, ellipsoid, about 2.6 cm. long and 1.6 cm. in diameter; cup thick-walled, cylindrical, covering about ⅕ of the acorn, about 8 mm. deep and 1.7 cm. in diameter, with the outer surface being rough with glabrous tuberculate scales.

I claim:

1. A new and distinct variety of English oak tree of the species botanically known as *Quercus robur,* substantially as herein shown and described, characterized particularly as to novelty by the unique combination of an expansive tree with a broadly hemispherical crown having a height/width ratio of 0.76; main scaffold branches all arising in the lower third of the crown, trending upward at about 60° from the vertical; the upper two-thirds of the trunk bearing only small branches and thus playing a minor role in the structural framework of the crown; sturdy wide-angle crotches averaging about 66°; attractive leathery leaves with a faint waxy bloom and being bluish-green on both surfaces; and extremely heavy fruit production which, in some years, amounts to 200 pounds or more.

References Cited

New Illustrated Encyclopedia of Gardening, Everett, 1960, Greystone Press, pp. 1748–9 relied on.

ROBERT E. BAGWILL, Primary Examiner